(12) United States Patent
Block

(10) Patent No.: US 8,493,067 B2
(45) Date of Patent: Jul. 23, 2013

(54) MAGNETIC RESONANCE SYSTEM AND METHOD TO CREATE A MAGNETIC RESONANCE IMAGE DATA SET BY RADIAL SCANNING OF A MAGNETIC RESONANCE SYSTEM

(75) Inventor: Kai Tobias Block, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 298 days.

(21) Appl. No.: 13/070,962

(22) Filed: Mar. 24, 2011

(65) Prior Publication Data

US 2011/0234228 A1 Sep. 29, 2011

(30) Foreign Application Priority Data

Mar. 24, 2010 (DE) .......................... 10 2010 012 599

(51) Int. Cl.
*G01V 3/00* (2006.01)
(52) U.S. Cl.
USPC .......................................... 324/309; 324/318
(58) Field of Classification Search
USPC ............................ 324/300–322; 600/407–445
See application file for complete search history.

(56) References Cited

U.S. PATENT DOCUMENTS

| | | | |
|---|---|---|---|
| 6,946,837 B2 * | 9/2005 | Sorland .......................... | 324/307 |
| 7,023,207 B1 | 4/2006 | Gaddipati et al. | |
| 7,323,873 B2 | 1/2008 | Yamazaki | |
| 7,635,978 B2 * | 12/2009 | Takahashi et al. ............. | 324/309 |
| 2008/0231272 A1 | 9/2008 | Taniguchi et al. | |
| 2010/0164495 A1 | 7/2010 | Takizawa et al. | |
| 2010/0237864 A1 * | 9/2010 | Stemmer ........................ | 324/309 |
| 2011/0215804 A1 * | 9/2011 | Deimling et al. .............. | 324/307 |
| 2012/0081113 A1 * | 4/2012 | Grodzki .......................... | 324/309 |
| 2012/0313640 A1 * | 12/2012 | Pfeuffer ......................... | 324/309 |

OTHER PUBLICATIONS

"Simple Correction Method for *k*-Space Trajectory Deviations in MRI," Duyn et al., Journal of Magnetic Resonance, vol. 132 (1998) pp. 150-153.
"Robust Radial Imaging With Predetermined Isotropic Gradient Delay Correction," Speier et al., Proc. Intl. Soc. Mag. Reson. Med., vol. 14 (2006) pp. 2379.
"Centering the Projection Reconstruction Trajectory: Reducing Gradient Delay Errors," Peters et al., Magnetic Resonance in Medicine, vol. 50 (2003) pp. 1-6.
"Spiral Imaging Artifact Reduction: A Comparison of Two k-Trajectory Measurement Methods," Lechner et al., Journal of Magnetic Resonance Imaging, vol. 29 (2009) pp. 1485-1492.

* cited by examiner

*Primary Examiner* — Brij Shrivastav
(74) *Attorney, Agent, or Firm* — Schiff Hardin LLP

(57) ABSTRACT

In a magnetic resonance apparatus and method to generate an image data set by means of a radial scanning of a raw data set, at least one calibration measurement is implemented for at least one predetermined spoke of the radial scan, and a gradient moment difference between an assumed gradient moment and an actually applied gradient moment is determined along the at least one predetermined spoke. Readout of all spokes of the predetermined raw data set ensues by activating multiple magnetic field gradients in spatial directions in order to respectively read out scan points of a respective spoke. The position of each scan point of each spoke is corrected depending on the gradient moment difference, by the position of the respective scan point that is assumed based on the respective activated magnetic field gradients being shifted by the gradient moment difference.

13 Claims, 2 Drawing Sheets

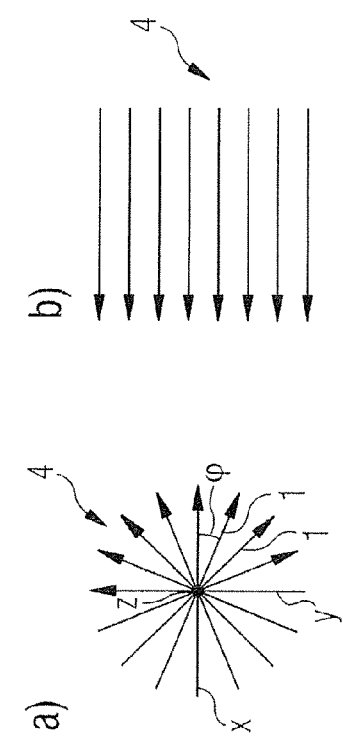
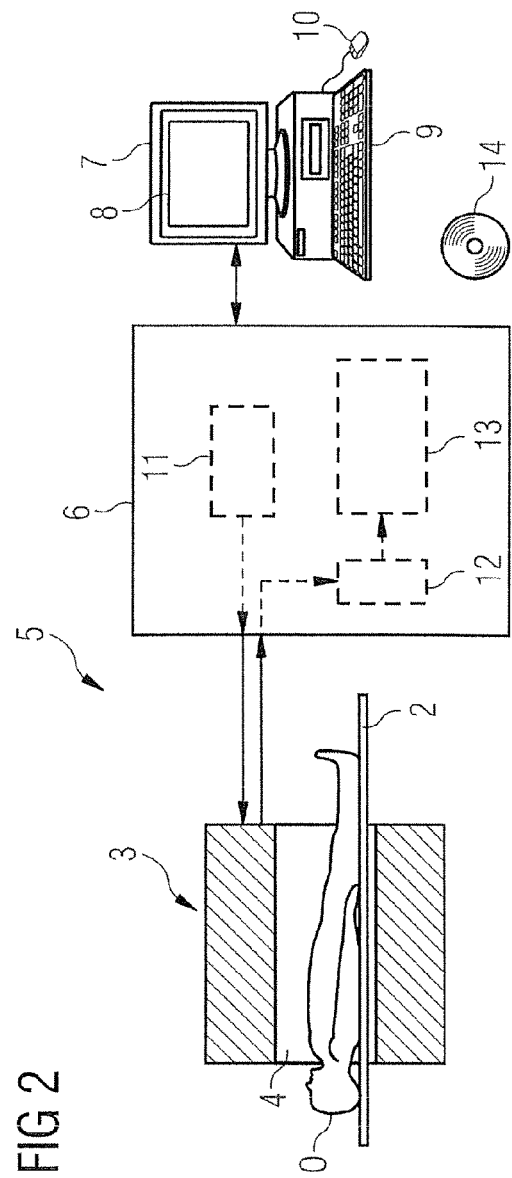
FIG 1
FIG 2

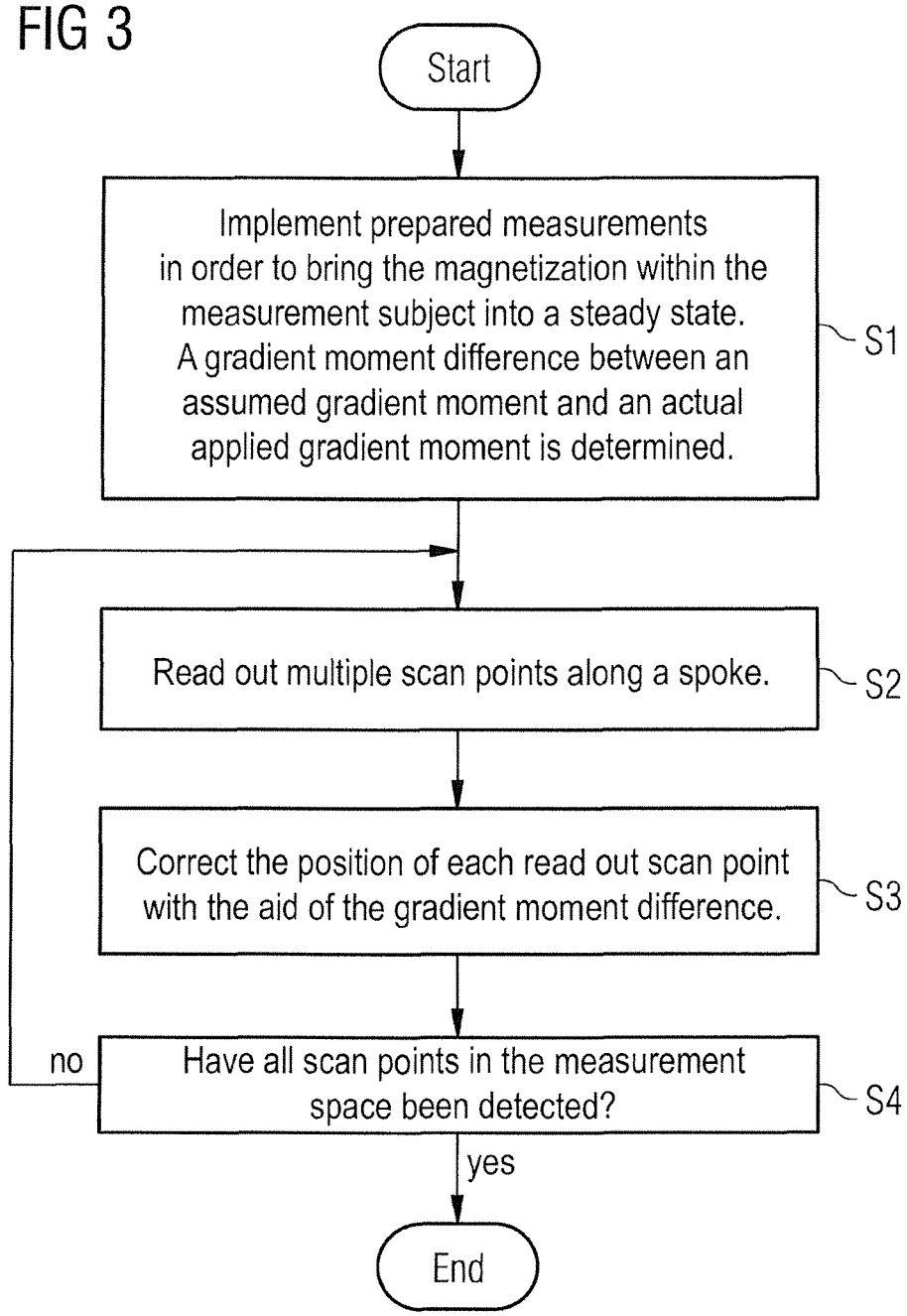

MAGNETIC RESONANCE SYSTEM AND METHOD TO CREATE A MAGNETIC RESONANCE IMAGE DATA SET BY RADIAL SCANNING OF A MAGNETIC RESONANCE SYSTEM

BACKGROUND OF THE INVENTION

1. Field of the Invention

The present invention concerns a method to create an image data set by radial scanning of a raw data space with the use of a magnetic resonance system, wherein unintended time delays of the gradient fields to be generated are corrected. Moreover, the present invention concerns a correspondingly designed magnetic resonance system.

2. Description of the Prior Art

In magnetic resonance tomography, a raw data space (also known as a measurement space or k-space) is typically scanned line by line. However, other scanning patterns are also known. In particular, radial scanning along spokes (i.e. straight lines running through the k-space center) has achieved increasing interest in recent years. Radial scanning offers different advantages, for example a reduced movement sensitivity and the possibility to scan with ultra-short echo times (UTE). Radial scanning is a method from the early days of magnetic resonance, a technique known for a very long time, but previously it could not be widely implemented. The causes of this are primarily inherent technical difficulties that arise upon transition of the scan trajectory along parallel lines to opposite, overlapping spokes.

Time delays of the gradient fields generated in the scanning that lead to a deviation between the assumed and the actual scanned coordinate of the Fourier-transformed data entries (i.e. in k-space) represent a core problem. In conventional, line-by-line scanning, these deviations are irrelevant since all lines are similarly shifted relative to the readout direction. Due to the shift property of the Fourier transformation (shift theorem), this shift leads to a linear phase modulation of the subject in image space with line-by-line scanning. However, since only the magnitude values (and not the phase) are typically considered in the imaging, in line-by-line scanning the phase modulation remains without effect on the presented image.

In radial scanning the gradient delays likewise lead to a linear phase modulation of the scanned components in image space. However, since the readout direction in each spoke differs from the readout direction of another arbitrarily different spoke, a different phase modulation of the contained spatial information respectively results. This different phase modulation leads to image artifacts that are strong in part due to interference effects that significantly reduce the diagnostic value of MR images created with radial scanning.

According to the prior art, no precise and conclusive insights about the physical causes of the gradient delays have existed. The structurally dependent response behavior of gradient coils appears to have a large influence since the observed gradient delays are for the most part anisotropic, meaning that the gradient delay of the gradient coil in the x-direction differs from the gradient delay of the gradient coil in the y-direction. Moreover, the gradient delays depend on the selected readout speed or bandwidth, which on the one hand could indicate an amplitude dependency or delays due to digitization hardware. Finally, there is an influence on eddy current effects and the system adjustment (shim settings).

According to the prior art, essentially two methods for correction of gradient delays are known. In the first method the actual generated gradient fields (and thus the trajectory generated in frequency space) are measured which are then subsequently used for the association of the measurement data in frequency space. For the trajectory measurements that are necessary, according to the prior art the two following documents with regard to the first method are known, which in part use special sensor hardware for the trajectory measurements.

"Simple Correction Method for k-Space Trajectory Deviations in MRI", J. H. Duyn, Y. Yang, J. A. Frank and J. W. van der Veen, JMR Volume 132, Issue 1, May 1998, Pages 150-153.

"Spiral imaging artifact reduction: A comparison of two k-trajectory measurement methods", S. M. Fechner, P. T. Sipilä, F. Wiesinger, A. B. Kerr, M. W. Vogel, JMRI Volume 29, Issue 6, Pages 1485-1492.

In the second method the time shift to be expected is estimated and the moment of the dephasing gradient is adapted depending on this such that the actual echo point in time (scanning of the origin position of the frequency space) coincides with the assumed echo time. This method is presented in "Centering the Projection Reconstruction Trajectory Reducing Gradient Delay Errors"; D. C. Peters, J. A. Derbyshire, E. R. McVeigh, Magn Reson Med., July 2003, 50(1): 1-6, wherein the delay for a fixed measurement protocol is determined with a one-time calibration measurement.

In "Robust radial imaging with predetermined isotropic gradient delay correction, P. Speier, F. Trautwein, Proc. Intl. Soc. Mag. Reson. Med. 14 (2006) 2379, the delay to be expected is determined using a linear model so that it is not necessary to conduct a new calibration given a change of the measurement parameters. However, in practice it has been shown that the corresponding correction is not sufficient since the original are apparently system-dependent, adjustment-dependent and also patient-dependent in part. The resulting image quality is therefore not sufficient for a clinical use, in particular not for morphological examinations.

SUMMARY OF THE INVENTION

An object of the present invention is to correct gradient delays in a radial scan better than this is possible according to the prior art.

Within the scope of the present invention, a method to create an image data set with a radial scanning by means of a magnetic resonance system includes the following steps:

For one or more predetermined spokes, one or multiple calibration measurements is/are implemented. In each calibration measurement, a gradient moment difference is determined between an assumed gradient moment and an actual, applied gradient moment along the respective spoke. Since the assumed or actually applied gradient moment corresponds to the assumed or actually scanned scan point in frequency space, the pixel shift between the assumed scan point and the actual scan point that results due to the gradient delay can be determined in k-space or frequency space at any time from the gradient moment difference.

All spokes of a predetermined raw data set are subsequently read out, wherein multiple magnetic field gradients are switched in a respective spatial direction (meaning two magnetic field gradients to read out one slice or three magnetic field gradients to read out one three-dimensional spatial segment) in order to acquire respective scan points of a respective spoke.

After the readout of the corresponding scan point, a position of each scan point of each spoke is corrected depending on the gradient moment difference. For this the assumed position of the respective scan point which is defined by the respective switched magnetic field gradients is shifted by the gradient moment difference.

The method according to the invention enables a practical use of a radial scan since the unwanted time delays of the generated gradient fields are corrected in the determination of the actual position of the respective scan point.

There are multiple possibilities to determine the gradient moment difference.

1. The gradient moment difference is determined only using precisely one predetermined spoke. For this an arbitrary spoke can be selected; however, the spoke is most often selected in the direction of the two or three gradient coils.

2. The gradient moment difference is determined using multiple predetermined spokes. Given this possibility the number of predetermined spokes normally corresponds to the number of magnetic field gradients or the gradient coils, wherein one of these two or three spokes respectively extends in the direction of the respective magnetic field gradients or in the direction of the respective gradient coil. However, it is also possible that the number of predetermined spokes exceeds the number of magnetic field gradients or gradient coils. Given this possibility the gradient moment difference is calculated as the average value of those gradient moment differences which have been determined for the predetermined spokes.

3. The number of predetermined spokes using which the gradient moment difference is determined corresponds to the number of magnetic field gradients or gradient coils. One of these two or three spokes thereby respectively extends in the direction of the respective magnetic field gradients or of the respective gradient coil. For each spoke a gradient moment difference is determined so that the gradient moment difference is essentially composed of two or three components.

While the possibilities 1 and 2 enable only an isotropic correction of the gradient delays, the possibility 3 also enables an anisotropic correction. Naturally, given all previously described possibilities it is possible that the gradient moment difference is determined repeatedly for the respective predetermined spoke in order to then work with an average value of these gradient moment differences as the gradient moment difference for this spoke.

In the embodiment according to the invention that is described in the following, an isotropic correction takes place, meaning that the gradient moment difference is determined according to the previously described possibilities 1 or 2. It is assumed that the assumed position of a scan point is defined by an x-coordinate $k'_x$ and by a y-coordinate $k'_y$, and the corrected position is defined by an x-coordinate $k_x$ and by a y-coordinate $k_y$. Depending on the gradient moment difference GMD and the angle $\phi$ which is present between the respective spoke at which the scan point lies and the x-axis, the x-coordinate $k_x$ of the corrected position is then calculated from the x-coordinate $k'_x$ of the assumed position according to Equation (1) and the y-coordinate $k_y$ of the corrected position is then calculated from the y-coordinate $k'_y$ of the assumed position according to Equation (2).

$$k_x = k'_x - GMD \times \cos(\phi) \quad (1)$$

$$k_y = k'_y - GMD \times \sin(\phi) \quad (2)$$

In other words, in this embodiment the assumed position of the respective scan point is shifted by the gradient moment difference along the spoke at which the scan point is located.

The gradient moment difference GMD can be converted into a pixel shift PV via the following Equation (3).

$$PV = \frac{GMD \times N}{2 \times k'_{max}} \quad (3)$$

N stands for the number of scan points along a spoke and $k'_{max}$ stands for the maximum assumed gradient moment. The delay is accordingly determined in the form of a pixel or sample shift. For example, a pixel shift PV of 2 means that the echo center lies within 2 sample intervals of the assumed echo position.

The pixel shift or echo shift can be used in an image reconstruction in order to compensate for errors in the position determination of the scan points. Similar to as in Equations (1) and (2), the radial trajectories require a special reconstruction method which is also known as a "gridding", wherein the measurement data are interpolated from the respective spoke positions on a regular grid. For this the position of the individual scan points is calculated in frequency space according to the following Equations (4) and (5).

$$k_x = (-k_{max} + i \times \Delta k) \times \cos(\phi) \quad (4)$$

$$k_y = (-k_{max} + i \times \Delta k) \times \sin(\phi) \quad (5)$$

$k_{max}$ thereby stands for a maximum gradient moment corrected by the gradient moment difference, i stands for the respective index of the scan position (meaning that i runs from 0 to N) and $\Delta k$ is the difference between the gradient moment of a scan point and the gradient moment of that scan point which is directly adjacent to it. $\Delta k$ is accordingly calculated by the following Equation (6):

$$\Delta k = \frac{2 \times k'_{max}}{N} \quad (6)$$

In order to consider the gradient delay in Equations (4) and (5), via the following Equation (7) the outer position $\pm k_{max}$ of the respective spoke is essentially shifted by the determined delay or pixel shift PV.

$$k_{max} = \Delta k \times \left(\frac{N}{2} + PV\right) \quad (7)$$

If the positions of the scan points in k-space are determined with Equations (4) through (7), the measurement data acquired at the corresponding scan points are associated with grid positions which approximately coincide with the actual frequency space positions at the scan point in time, meaning that gradient delays are thereby taken into account or corrected.

The embodiments described in the preceding with which the corrected positions of the scan points are determined apply for a two-dimensional radial scan. The present invention is naturally also applicable for a three-dimensional radial scan. In this case three equations are required to determine the coordinates $k_x$, $k_y$, $k_z$. Equation (7) maintains its validity in an isotropic correction.

In the following an embodiment according to the invention is described to determine the gradient moment difference along one of the predetermined spokes. For this a first signal $S_0(t)$ is read out along this spoke in a predetermined direction (there are only two possibilities for this direction, namely the forward direction and the reverse direction along the spoke)

over a predetermined length of this spoke. Moreover, a second signal $S_{180}(t)$ is read out along this spoke in a direction opposite the predetermined direction (thus in the other direction) over the same length.

If the x-axis is placed along this spoke, the first signal $S_0(t)$ corresponds to a measurement with the angle 0° and the second signal $S_{180}(t)$ corresponds to a measurement with the angle 180°. If no gradient shift exists, the first signal $S_0(t)$ is merely exchanged or inverted with the second signal $S_{180}(t)$ with regard to the order. In other words, the two signals are identical if the sorting of the acquired values of the second signal $S_{180}(t)$ is reversed. If an additional second signal $S'_{180}(t)$ is now defined according to the following Equation (8) in which the order of the samples is exchanged or inverted with regard to the second signal $S_{180}(t)$, this additional second signal $S'_{180}(t)$ is then equal to the first signal $S_0(t)$ if no gradient delay is present.

$$S'_{180}(t) = S_{180}(N-1-t) \quad (8)$$

with N equal to the number of samples (i.e. t=0, 1, ..., N−1) on the corresponding spoke or, respectively, in this case on the x-axis.

However, if a gradient shift is present, double the pixel shift (2×PV) exists between the two signals $S_0(t)$ and $S'_{180}(t)$ so that the following Equation (9) applies.

$$S_0(t) = S'_{180}(t + 2 \times PV) \quad (9)$$

In other words, since both the first signal $S_0(t)$ and the additional second signal $S'_{180}(t)$ are delayed, the echo delay or pixel shift PV results from half of the pixel offset between the first signal $S_0(t)$ and the additional second signal $S'_{180}(t)$.

A cross-correlation analysis as is described in the following is implemented to determine the pixel shift PV from the calibration measurements.

In order to design the method according to the invention to be robust with regard to phase modulation, after the resorting the magnitude of the complex signals $S_0(t)$ and $S'_{180}(t)$ is initially calculated. The Fourier transform of the magnitudes for both signals is subsequently calculated. By the shift property of the Fourier transformation that was already addressed in the preceding, the pixel offset of $S'_{180}(t)$ is translated into a phase modulation with regard to the Fourier transform of $S_0(t)$. This phase modulation is determined in that the Fourier-transformed magnitude of $S_0(t)$ is multiplied with the complexly conjugated Fourier-transform of the magnitude of $S'_{180}(t)$, whereby a function g(x) according to Equation (10) results.

$$g(x) = FT(|S_0(t)|) \times \text{Conj}(FT(|S'_{180}(t)|)) \quad (10)$$

The gradient moment difference with regard to this spoke can now be determined depending on this function g(x).

According to a first approach according to the invention, for this the inverse Fourier transformation of g(x) is determined, whereby the cross-correlation function of $S_0(t)$ and $S'_{180}(t)$ is obtained. A distance between the position of the maximum of this cross-correlation function invFT(g(x)) and the k-space center corresponds to twice the pixel shift 2×PV.

According to a second approach according to the invention, the slope of the phase curve is determined by g(x). In the case of a simple (i.e. similar) delay along the spoke, this phase curve is purely linear. However, since the measurement space is normally larger than the measurement subject, the phase of g(x) is determined only within the measurement subject. In order to account for this fact, in a first step the measurement maximum of g(x) is determined. Assuming this maximum, an interval is determined such that the magnitude of g(x) at this interval in which the maximum is also located is never smaller than a predetermined magnitude threshold. This magnitude threshold is thereby a predetermined percentage (for example 5%) less than the magnitude maximum. Within this interval, a linear function is subsequently adapted (fitted) to the phase curve of g(x), for example with a linear compensation calculation. The pixel shift PV then results from the slope S of the linear function or, respectively, straight line according to the following Equation (11).

$$PV = -S \times \frac{N}{4 \times \Pi} \quad (11)$$

With the use of Equation (3), the gradient moment difference GMD along the spoke can be determined from this according to the following Equation (12).

$$GMD = -S \times \frac{k'_{max}}{2 \times \Pi} \quad (12)$$

In order to implement an anisotropic correction of the delay, given a two-dimensional radial scan a calibration measurement along the x-axis is implemented to determine the gradient moment difference $GMD_x$ along the x-axis and a calibration measurement along the y-axis is implemented to determine the gradient moment difference $GMD_y$ along the y-axis. Given a three-dimensional radial scan, a calibration measurement would additionally have to be implemented along the z-axis to determine the gradient moment difference $GMD_z$ along the z-axis. Via Equation (3) the corresponding gradient moment difference $GMD_x$, $GMD_y$ or, respectively, $GMD_z$ can simply be converted into the corresponding pixel shift $PV_x$, $PV_y$ or, respectively, $PV_z$. For anisotropic correction, Equation (7) is now replaced with the following Equation (13).

$$k_{max} = \frac{N}{2} + \frac{(\cos(2 \times \varphi) + 1) \times PV_x + (-\cos(2 \times \varphi) + 1) \times PV_y}{2} \quad (13)$$

The anisotropically corrected position of the corresponding scan point can then be determined via Equations (4) and (5) under consideration of Equation (13).

However, it is also possible to determine the corrected position $(k_x, k_y)$ of the scan point according to the following Equations (14) and (15) from the assumed position $(k'_x, k'_y)$ of the respective scan point depending on the gradient moment differences $GMD_x$ and $GMD_y$.

$$k_x = k'_x - \frac{((\cos(2 \times \varphi) + 1) \times GMD_x + (-\cos(2 \times \varphi) + 1) \times GMD_y)}{2} \times \cos(\varphi) \quad (14)$$

$$k_y = k'_y - \frac{((\cos(2 \times \varphi) + 1) \times GMD_x + (-\cos(2 \times \varphi) + 1) \times GMD_y)}{2} \times \sin(\varphi) \quad (15)$$

An anisotropic gradient delay can lead to the situation that spokes which are generated by a superimposition of the X- and Y-gradients (and possibly with a superimposition of the Z-gradient in the three-dimensional case) are offset relative to the k-space center. This shift relative to the k-space center can be corrected via the embodiments described previously with Equations (13) through (15).

The implementation of the calibration measurements to determine the gradient moment differences or pixel shifts can be implemented in a preparation phase of the actual MR measurement. In particular in gradient echo-based measurement sequences which use a short repetition time (for example 3D FLASH or 2D FLASH), it is typically required that what are known as "prep shots" are implemented before the acquisition of the actual measurement data so that the magnetization is brought into a steady state within the measurement subject. These preparatory measurements are important in radial sequences since all spokes contribute equally important information (measurement data) to the total result, such that the information acquired over the first spokes is also important for the total result. If no preparatory measurements (prep shots) are implemented, the signal strength in the measurements of the first spoke is too high due to the as of yet not present saturation of the magnetization in the measurement subject, which leads to what are known as smearing artifacts.

For example, with 200 prep shots, 100 gradient moment differences can be calculated along one spoke. Since essentially only the spokes along the x-gradient coil and along the y-gradient coil are of interest in a two-dimensional radial scan, the gradient moment difference along the x-axis and the gradient moment difference along the y-axis can thus be respectively determined 50 times. The ultimate gradient moment difference along the x-axis and the ultimate gradient moment difference along the y-axis are then calculated by an average value calculation. For this purpose there is, for example, the possibility to average the acquired signals (for example $S_0(t)$, $S_{180}(t)$) and then to determine the ultimate gradient moment difference using these averaged signals. The other possibility is to determine the respective gradient moment difference from two respective corresponding signals (for example $S_0(t)$, $S_{180}(t)$) and then to determine the ultimate gradient moment difference via average value calculation from these (for example 50) gradient moment differences.

Any of the above-described embodiments of the method according to the invention can be combined to pre-compensate the gradient delay by adapting the moment of the pre-dephasing gradient (see D. C. Peters et al. or P. Speier et al.). The present invention then in particular corrects those delays of the gradient fields which are still present in spite of the adapted pre-dephasing gradients.

Within the scope of the present invention, a magnetic resonance system is also provided to create an image data set by means of a radial scan. The magnetic resonance system includes an activation unit (control unit) to activate a scanner (data acquisition unit) of the magnetic resonance system, a receiver device to receive signals acquired by the tomograph and an evaluation device to evaluate the signals and to create the image data set. The magnetic resonance system is designed such that the magnetic resonance system implements one or more calibration measurements for one or more predetermined spokes in order to determine a gradient moment difference along the one or more spokes. The magnetic resonance system reads out all spokes of the raw data set in that the magnetic resonance system in that the magnetic resonance system switches multiple magnetic field gradients in a respective spatial direction in order to read out respective scan points of one of these spokes. The magnetic resonance system corrects a position of each scan point of each spoke depending on the gradient moment difference in that the magnetic resonance system shifts a position of the respective scan point (assumed based on the respective switched magnetic field gradient) by the gradient moment difference.

The advantages of the magnetic resonance system according to the invention essentially correspond to the advantages of the method according to the invention.

Furthermore, the present invention describes a non-transitory computer-readable storage medium embodying a computer program or software, which can be loaded into a memory of a programmable controller or a computer (or computer system) of a magnetic resonance system. All or various embodiments of the method according to the invention that are described in the preceding can be executed with this computer program when the computer program runs in the controller. The computer program may require peripheral items (for example libraries and auxiliary functions) in order to realize the corresponding embodiments of the method. The software can be a source code (for example C++) that must still be compiled and linked or must only be interpreted, or can be executable software code that only needs to be loaded into the corresponding computer for execution.

The electronically readable storage medium may be, for example a DVD, a magnetic tape or a USB stick on which is stored electronically readable control information, in particular software (see above). When this control information (software) is read from the data medium and stored in a controller or computer of a magnetic resonance system, all embodiments of the method described in the preceding can be implemented.

The present invention is advantageously adaptive, requires no user interaction and requires no preceding calibration steps so that the measurement time is not extended. The present invention advantageously corrects apparatus-specific and patient-dependent delays which, according to the prior art, represent a clear problem for the routine use of radial measurement techniques.

The present invention is particularly suitable for MR methods that operate with a radial scanning. MR methods in which a spoke is scanned in multiple steps, i.e. with multiple RF excitations, also fall under this category. The present invention is naturally not limited to these preferred application fields since the present invention could also be used in single point imaging, for example.

BRIEF DESCRIPTION OF THE DRAWINGS

FIGS. 1a and 1b schematically illustrates radial scanning and a line-by-line scanning.

FIG. 2 schematically illustrates a magnetic resonance system according to the invention.

FIG. 3 is a flow chart of an embodiment of the method according to the invention.

DESCRIPTION OF THE PREFERRED EMBODIMENTS

A radial scanning is shown in FIG. 1a and a conventional line-by-line scanning is shown in FIG. 1b. In the conventionally used line-by-line scanning, a measurement space 4 or a slice of k-space is scanned line by line, wherein multiple points are acquired per line. The scanned slice is thereby scanned uniformly in both the horizontal and vertical directions. This means that scan points for the most part have the same distance from their neighbors in the horizontal and vertical direction.

In contrast to this, in the two-dimensional radial scanning shown in FIG. 1a the measurement space 4 or the scanned slice are scanned by means of spokes 1 which, like the spokes of a wheel, run through the center Z of the slice. Multiple points which are normally arranged equidistantly on the spoke 1 are thereby detected for each spoke 1. Given a radial scanning, more scan points are therefore detected in the region around the center Z than in the boundary regions of the measurement space 4.

For orientation, in FIG. 1a a spoke x is characterized as an x-axis and a spoke y situated perpendicular to this is characterized as a y-axis. This designation is voluntary, meaning that two arbitrary spokes 1 standing perpendicular to one another are characterized as x-axis and y-axis. An angle φ designates that angle which encloses the corresponding spoke 1 with the x-axis.

Given a three-dimensional radial scanning, the spokes 1 would likewise run through the same center. However, in this case the spokes are not arranged in a plane but rather such that their ends lie on a type of spherical surface, wherein the center is the middle point of the associated sphere.

A magnetic resonance system 5 according to the invention is schematically shown in FIG. 2. The magnetic resonance system 5 essentially comprises: a scanner 3 with which the magnetic field necessary for the MR examination is generated in a measurement space 4; a table or recumbent board 2; a control device 6 with which the scanner 3 is controlled and MR data are detected by the scanner 3; and a terminal 7 connected to the control device 6.

The control device 6 has an activation unit 11, a receiver device 12 and an evaluation device 13. During the creation of an image data set, MR data are acquired by means of the scanner 3 from the receiver device 12, wherein the scanner 3 and the table 2 are activated by the activation unit 11 such that MR data are acquired in a measurement volume which is located inside the body of a patient O lying on the table 2.

The evaluation device 13 then prepares the MR data such that they can be graphically presented on a screen 8 of the terminal 7, and such that images according to the invention in which delays of the generated gradient fields are corrected are displayed. In addition to the graphical presentation of the MR data, with the terminal 7 (which comprises a keyboard 9 and a mouse 10 in addition to the monitor 8) a three-dimensional volume segment to be measured or an essentially two-dimensional slice (for example) can be predetermined by a user and additional parameters for implementation of the method according to the invention can be determined. The software for the control device 6 can also be loaded into the control device 6 via the terminal 7. This software of the control device 6 can thereby also comprise the method according to the invention. It is also possible that a method according to the invention is contained in a software which runs in the terminal 7. Independent of in which software the method according to the invention is contained, the software can also be stored on a DVD 14, such that this software can then be read from the DVD 14 by the terminal 7 and can be copied either into the control device 6 or into a computer of the terminal 7.

A flow chart of a method according to the invention is depicted in FIG. 3.

What are known as prep shots are implemented in Step S1 in order to bring the magnetization within the measurement subject into a steady state. In these prep shots the gradient moment differences between an assumed gradient moment and an actually applied gradient moment are determined repeatedly for the spokes situated on the x-axis and on the y-axis by means of, for example, the approach according to the invention that is described with Equations (8) through (11).

Multiple scan points along the spokes 1 are scanned in Step S2. The position of every read-out scan point is subsequently corrected with the aid of the gradient moment difference(s) determined in Step S1. This correction in particular takes place with an approach according to the invention that is described with Equations (1) through (7) and (13) through (15).

In Step S4 it is checked whether all scan points in the measurement space have already been detected, i.e. whether all scan points of all spokes have been read out. If this is not the case (no in Step S4), the method returns to Step S2 in which still-missing scan points of an already-scanned spoke or scan points of an additional, not-yet-scanned spoke 1 are read out. If all scan points have already been detected (yes in Step S4), the method ends.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to create an image data set by radial scanning of a raw data space in a magnetic resonance system, comprising:
    operating the magnetic resonance system to conduct at least one calibration measurement for at least one predetermined spoke of the radial scan, and determining a gradient moment difference between an assumed gradient moment and an actually applied gradient moment along the at least one predetermined spoke;
    reading out all spokes of the predetermined raw data space by activating multiple magnetic field gradients in respective spatial directions in order to read out respective scan points of a respective spoke; and
    in a processor, automatically correcting a position of each scan point of each spoke depending on the gradient moment difference by shifting the position of the respective scan point that is assumed based on the respective switched magnetic field gradients by the gradient moment difference.

2. A method as claimed in claim 1 comprising operating said magnetic resonance system to implement said calibration measurement for only one predetermined spoke.

3. A method as claimed in claim 1 comprising operating said magnetic resonance system to implement said calibration measurement for multiple predetermined spokes, with a number of said multiple predetermined spokes being equal to a number of said magnetic field gradients and said multiple predetermined spokes respectively extending along respective directions of the magnetic field gradients.

4. A method as claimed in claim 3 comprising determining a spoke gradient moment difference for each of said multiple predetermined spokes, and determining said gradient moment difference as an average of said spoke gradient moment differences.

5. A method as claimed in claim 1 comprising:
    defining said assumed position of each scan point by an x-coordinate $k'_x$ and a y-coordinate $k'_y$,
    defining the corrected position of each scan point by an x-coordinate $k_x$ and a y-coordinate $k_y$;
    determining $k_x$ as $$k_x = k'_x - \text{GMD} \times \cos(\varphi); \text{ and}$$

determining $k_y$ as $$k_Y = k'_y - \text{GMD} \times \sin(\varphi),$$

wherein GMD is the gradient moment difference and φ is an angle between the respective spoke and the x-axis.

6. A method as claimed in claim 1 comprising determining the gradient moment difference along said predetermined one of said spokes by:

reading out a first signal $S_0(t)$ along said predetermined one of said spokes in a predetermined direction along a predetermined length of said predetermined one of said spokes;

reading out a second signal $S_{180}(t)$ along said predetermined one of said spokes in a direction opposite to said predetermined direction, over said predetermined length;

determining an additional second signal $S'_{180}(t)$ along said predetermined one of said spokes from said second signal $S_{180}(t)$, by reversing an order of scan values in said second signal $S_{180}(t)$, to produce said additional second signal $S'_{180}(t)$;

determining a function g(x) by Fourier-transforming a magnitude of said first signal $S_0(t)$ and multiplying the Fourier-transformed magnitude with a complex conjugated Fourier transform of the magnitude of the additional second signal $S'_{180}(t)$, according to $$g(x)=FT(|S_0(t)|) \times Conj(FT(|S'_{180}(t)|));\text{ and}$$

determining said gradient moment difference of said predetermined one of said spokes dependent on g(x).

7. A method as claimed in claim 6 comprising determining a location of a maximum of an inverse Fourier transform of g(x), and determining said gradient moment difference as a distance between said location of said maximum and a center of said raw data space.

8. A method as claimed in claim 6 comprising:
determining a maximum of a magnitude of g(x);
determining a magnitude threshold that is a predetermined percentage less than said magnitude maximum of g(x);
determining a contiguous region of g(x) in which said magnitude maximum lies and in which the magnitude of g(x) is not less than said magnitude threshold;
in said contiguous region, adapting a straight line to a phase curve of g(x) and determining a slope S of said straight line; and
determining the gradient moment difference GMD as $$GMD = -S \times \frac{k'_{max}}{2\Pi},$$

wherein $k'_{max}$ is the maximum gradient moment.

9. A method as claimed in claim 1, comprising:
operating said magnetic resonance system to implement said calibration measurement along the x-axis (x), and determining a gradient moment difference $GMD_x$ between an assumed scan point and an actually scanned scan point on the x-axis (x);
operating the magnetic resonance system to also implement said calibration measurement along the y-axis (y), and determining a gradient moment difference $GMD_y$ between an assumed scan point and an actually scanned scan point on the y-axis (y);
defining the assumed position by an x-coordinate $k'_x$ and a y-coordinate $k'_y$;
defining the corrected position by an x-coordinate $k_x$ and a y-coordinate $k_y$; and
determining the x-coordinate $k_x$ of the corrected position as $$k_x = k'_x - \frac{((\cos(2\times\varphi)+1)\times GMD_x + (-\cos(2\times\varphi)+1)\times GMD_y)}{2} \times \cos(\varphi),$$

and determining the y-coordinate $k_y$ of the corrected position as $$k_y = k'_y - \frac{((\cos(2\times\varphi)+1)\times GMD_x + (-\cos(2\times\varphi)+1)\times GMD_y)}{2} \times \sin(\varphi),$$

wherein φ is an angle between the at least one predetermined spoke and the x-axis.

10. A method as claimed in claim 1 comprising operating gradient coils of said magnetic resonance system to activate said magnetic field gradients, before reading out all of said spokes of said raw data space, operating said magnetic resonance system to implement prepared measurements that bring a magnetization of said gradient coils into a steady state, and implementing the calibration measurement with the gradient coils in said steady state.

11. A method as claimed in claim 1 comprising:
in said processor, estimating an estimated gradient moment difference; and
operating said magnetic resonance system in said calibration measurement by activating a pre-casing gradient having said estimated gradient moment difference with said estimated gradient moment difference corrected by said pre-phasing gradient.

12. A magnetic resonance system comprising:
a magnetic resonance system that conducts at least one calibration measurement for at least one predetermined spoke of the radial scan, and determining a gradient moment difference between an assumed gradient moment and an actually applied gradient moment along the at least one predetermined spoke;
said magnetic resonance system reading out all spokes of the predetermined raw data space by activating multiple magnetic field gradients in respective spatial directions in order to read out respective scan points of a respective spoke; and
a processor configured to automatically correct a position of each scan point of each spoke depending on the gradient moment difference by shifting the position of the respective scan point that is assumed based on the respective switched magnetic field gradients by the gradient moment difference.

13. A non-transitory computer-readable storage medium encoded with programming instructions, said storage medium being loaded into a computerized control and processing system of a magnetic resonance system that also includes a magnetic resonance data acquisition unit, and said programming instructions causing said computerized control and processing system to:
operate the magnetic resonance data acquisition unit to conduct at least one calibration measurement for at least one predetermined spoke of the radial scan, and determining a gradient moment difference between an assumed gradient moment and an actually applied gradient moment along the at least one predetermined spoke;
read out all spokes of the predetermined raw data space by activating multiple magnetic field gradients in respective spatial directions in order to read out respective scan points of a respective spoke; and
automatically correct a position of each scan point of each spoke depending on the gradient moment difference by shifting the position of the respective scan point that is assumed based on the respective switched magnetic field gradients by the gradient moment difference.

* * * * *